United States Patent [19]

van Duyn

[11] Patent Number: Plant 6,757

[45] Date of Patent: Apr. 25, 1989

[54] ALSTROEMERIA NAMED CORDU JOY

[75] Inventor: Cornelis van Duyn, Rijnsburg, Netherlands

[73] Assignee: Groot Associates II, Irvine, Calif.

[21] Appl. No.: 57,232

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the deep red colored blossoms, the petals of which are reddish orange with an orange yellow striped heart. The plant is early in flowering with relatively short stems.

1 Drawing Sheet

BACKGROUND OF THE NEW PLANT

This new Alstroemeria originated as a sport at Rijnsburg, Holland. The particular sport was selected from plants propagated via root division by me in 1979 for propagation and testing because of the distinctive coloration of its blossoms produced on upright compact stems. Specifically, the inner petals are reddish with slight orange yellow striped hearts. The outer petals are a solid deep red coloring. The inner petals have well defined longitudinal streaks or flecks of dark red. The selected plant was propagated by me at Rijnsburg, Holland through several generations of root divisions to establish that its distinctive characteristics hold true from generation to generation and appear to be firmly fixed.

Breeding efforts commenced in 1977 and propagation is currently being carried out at Rijnsburg, Holland. The nearest variety is the Alstroemeria called Red Valley and my new variety, Cordu Joy, differs from the Red Valley in that (1) the flowers are a much darker red with very little yellow in the center and (2) the flower stems are shorter and stronger.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material, #2107, comprising the ISCC-NBS Centroid Color Charts and NBS Special Publication, #440.

THE PLANT

Origin: Sport.
Parentage: Red Valley.
Classification: Alstroemeria hybrid.
Form: A generally erect bush having an upright stalk with flower-bearing branches in simple umbel arrangement at its top.
Height: About 0.80 cm.
Growth: Upright and normal.
Root stock: Mutation.
Foliage:
*Quantity.*—Normal.

*Number of leaves.*—About 15–20 per stem.
*Size of leaf.*—About 10.5 cm×3 cm.
*Shape of leaf.*—Parallel venation.
*Texture.*—Smooth.
*Color.*—Upper side: Light green. Under side: Light green.

THE BUD

Form: Long, ovoid.
Size: Medium.
*Diameter.*—About 1.2 cm.
*Length.*—About 2.5 cm.
Peduncle:
*Length.*—About 12 cm.
*Texture.*—Smooth.
*Form.*—Erect.

THE FLOWER

Blooming habit: Profusely during early season in Spring.
Flower size; Medium.
*Diameter.*—About 5 cm.
*Depth.*—About 4.5 cm.
Borne: Terminal clusters.
Shape: Generally cup shaped with petal tips curling outwardly.
Petalage:
*Number of petals.*—Six.
*Arrangement.*—Two concentric circles of three.
*Form.*—Broad ovate.
*Texture.*—Soft.
*Appearance.*—Velvety.
Color: Outer petals: Deep red (No. 13). Inner petals: Deep red (No. 13) with red orange (No. 35) fading to yellow (No. 68) center. The inner petals have numerous generally longitudinal stripes or flecks of dark purplish red (No. 17).
Persistence: The flowers hang on and dry
Main stem or stalk:
*Length.*—About 12 cm.
*Color.*—Green.
*Character.*—Strong and upright.
Lasting quality of flower: About 3 weeks. As a cut flower, about 10–14 days.

REPRODUCTIVE ORGANS

Stamens:
*Number.*—Six.
*Arrangement.*—One opposite each petal.

Anthers:

*Size.*—About 0.5 cm×0.2 cm.

*Color.*—Deep red (No. 16).

Filaments:

*Length.*—About 3.8 cm.

*Color.*—Soft red (No. 12).

*Pollen.*—Yellow Brown.

Pistils:

*Number.*—One.

*Styles.*—Length: About 3.9 cm. Color: Soft red (No. 12).

Fruit:

*Shape.*—Oblong.

*Color.*—Light brown.

This plant is particularly noted for the distinctive coloration of its flowers, which coloration does not clearly resemble that of any other Alstroemeria plant previously known to me. The dark red flecks on the strong orange yellow inner petals with the dark red striped hearts and outer petals with the solid deep red coloring make this plant an attractive addition to the Alstroemeria family.

I claim:

1. A new and distinctive Alstroemeria cultivar, substantially as herein shown and described, characterized by the distinctive coloration of its medium and profusely blooming flowers.

* * * * *

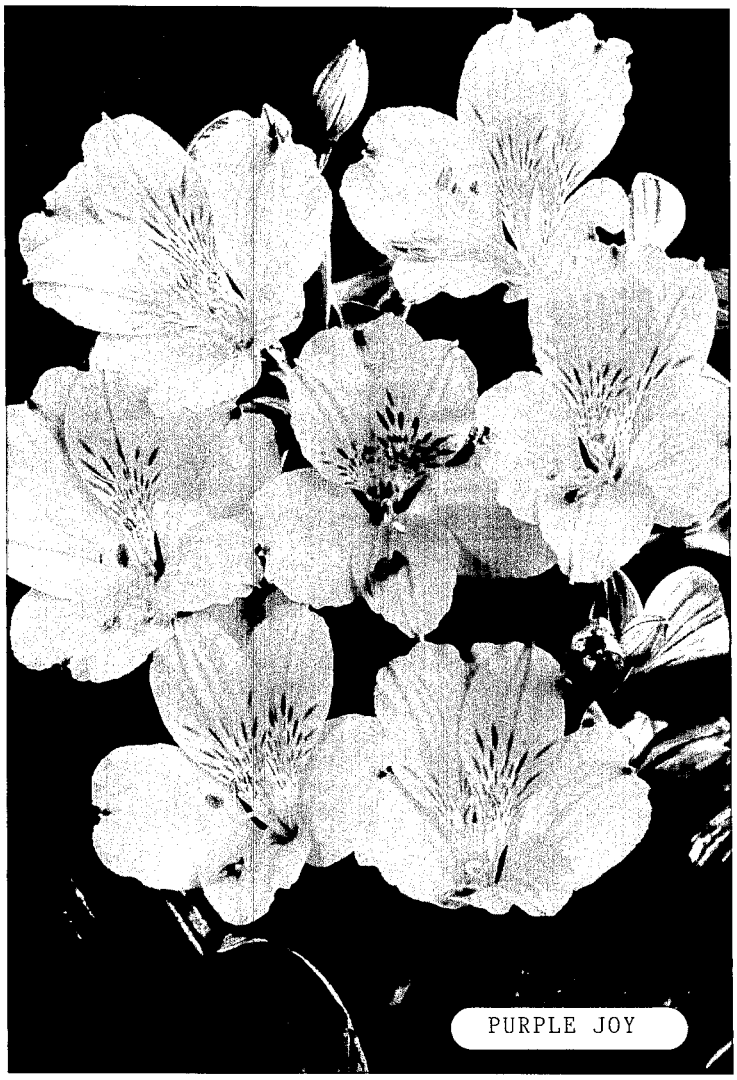

U.S. Patent Apr. 25, 1989 Plant 6,757